United States Patent

Hamada et al.

[11] Patent Number: 4,555,513
[45] Date of Patent: Nov. 26, 1985

[54] 1,2 DIHYDRO- AND 1,2,3,4-TETRAHYDRO QUINOLYLACETIC ACIDS AND ANALGESIC USE THEREOF

[75] Inventors: Masaaki Hamada; Kaoru Okamaoto; Teikichi Kurosaki, all of Osaka, Japan

[73] Assignee: Nippon Zoki Pharmaceutical Co., Osaka, Japan

[21] Appl. No.: 452,146

[22] Filed: Dec. 22, 1982

[30] Foreign Application Priority Data

Dec. 29, 1982 [JP] Japan .................. 56-211626

[51] Int. Cl.⁴ .................. A61K 31/47; C07D 215/06
[52] U.S. Cl. .................. 514/311; 548/165
[58] Field of Search .................. 546/165; 424/258; 514/311

[56] References Cited

FOREIGN PATENT DOCUMENTS 2278338  2/1976  France .
1265648  3/1972  United Kingdom .
2001959  2/1979  United Kingdom .

OTHER PUBLICATIONS

Chemical Abstracts, vol. 64, No. 12, Abstract No. 17538C, 6/66.
Chemical Abstracts, vol. 69, No. 11, Abstract No. 43814K, 9/68.
Chemical Abstracts, vol. 70, No. 3, Abstract No. 10292F, 1/69.

*Primary Examiner*—Richard L. Raymond
*Assistant Examiner*—D. B. Springer
*Attorney, Agent, or Firm*—Pennie & Edmonds

[57] ABSTRACT

Novel quinolylacetic acid compounds of the formula (I):

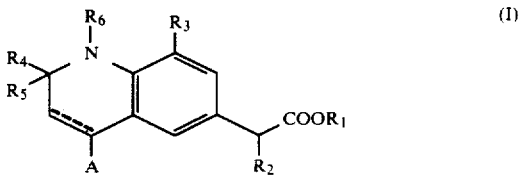

wherein
$R_1$ is a member selected from the group consisting of hydrogen atom, a lower alkyl group having 1 to 4 carbon atoms, and a lower alkyl group having 1 to 4 carbon atoms substituted with an aromatic group having a substituent;
$R_2$ is a member selected from the group consisting of hydrogen atom and a lower alkyl group having 1 to 4 carbon atoms;
$R_3$ is a member selected from the group consisting of hydrogen, a halogen atom, an alkyl group having 1 to 8 carbon atoms, and an alkenyl group having 2 to 8 carbon atoms;
$R_4$ and $R_5$, carpable of cyclization, are each a member selected from the group consisting of hydrogen atom and a lower alkyl group having 1 to 4 carbon atoms;
$R_6$ is a member selected from the group consisting of hydrogen atom an alkyl group having 1 to 8 carbon atoms, an alkenyl group having 2 to 5 carbon atoms, an alkynyl group having 3 to 8 carbon atoms, an aralkyl group, a substituted aralkyl group, an aliphatic or aromatic acyl group, and a substituted aliphatic or aromatic acyl group; and
A is a member selected from the group consisting of hydrogen atom and an oxo group;

the broken line denoting a second bond or no bond when A is a hydrogen atom and denoting no bond when A is an oxo group, and pharmaceutically acceptable salts thereof.

19 Claims, 1 Drawing Figure

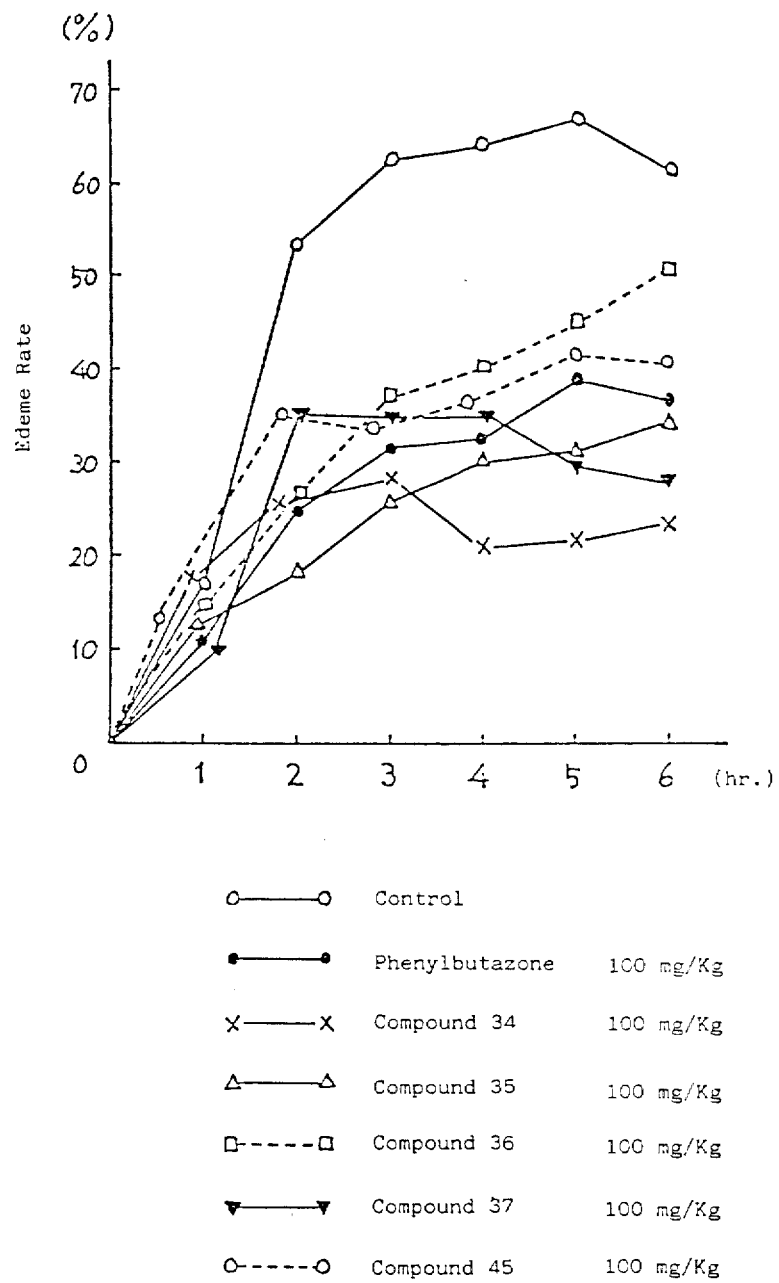

1,2 DIHYDRO- AND 1,2,3,4-TETRAHYDRO QUINOLYLACETIC ACIDS AND ANALGESIC USE THEREOF

DETAILED DESCRIPTION OF THE INVENTION

This invention relates to new quinolylacetic acid compounds and pharmaceutical compositions containing such compounds.

Although compounds such as salicylates, anthranilic acid derivatives, phenylacetic acid derivatives, indolylacetic acid derivatives and pyrazolones have been used conventionally as drugs having antipyretic, analgesic and antiinflammatory actions, they have given rise to troubles due to side effects such as gastro-intestinal, hepatorenal and hematological disorders. Alleviation of these adverse effects has been intended by improving dosage forms and by chemical modification, or more recently by other methods e.g. the use of pro-drugs.

The present invention results from investigation for drugs comparable or superior to conventional non-steroid drugs in effectiveness, and without the above-mentioned side effects. As a result, some types of new quinolylacetic acid compounds were discovered, and certain of these compounds were found to have antiinflammatory and antipyretic-analgesic actions, as well as low toxicity, showing pharmaceutically useful compounds. Thus the present invention was completed.

The object of this invention is to provide new heterocyclic compounds useful as therapeutic agents and their production as well as pharmaceutical compositions containing the invented compounds as effective ingredients and the method of application thereof.

The compounds included in this invention are represented by the following general formula (I).

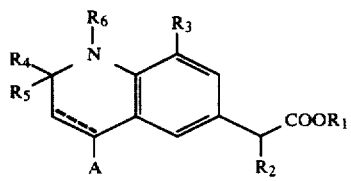

in which $R_1$ is a hydrogen atom or a lower alkyl group (which may optionally be substituted with aromatic group having substituent), $R_2$ is a hydrogen atom or a lower alkyl group, $R_3$ is a hydrogen, halogen atom or an alkyl or alkenyl group, each of $R_4$ and $R_5$ is a hydrogen atom or a lower alkyl group (which may optionally form a ring by cyclization of $R_4$ and $R_5$), $R_6$ is a hydrogen atom or an alkyl, alkenyl, alkynyl group, an aralkyl or acyl group which may optionally have a substituent, A is a hydrogen atom or an oxo group, when A is a hydrogen atom, the broken line is a second bond or no bond bond, when A is an oxo group, the broken line is no bond, and the compounds that are pharmacologically acceptable salts thereof.

Values of $R_1$ include a hydrogen atom, or straight or branched lower alkyl group having 1 to 4 carbon atoms, such as methyl, ethyl, propyl, iso-propyl, butyl, iso-butyl, sec-butyl, t-butyl group, which may optionally be substituted with an aromatic group substituted with a halogen, an alkyl or an alkoxy group, such as a phenyl group. $R_1$ also indicates any group which is able to form ester compounds with a free carboxylic acid of the present invention, such as an alkyl group which may optionally be substituted with trihalomethyl, cycloalkyl or aralkyl group or heterocyclic group which may optionally have a substituent.

Values of $R_2$ include a hydrogen atom or straight or branched lower alkyl group having 1 to 4 carbon atoms similar to $R_1$.

Values of $R_3$ include a hydrogen atom; a halogen atom such as fluorine, chlorine, bromine, iodine; straight or branched alkyl group preferably having 1 to 8 carbon atoms such as methyl, ethyl, propyl, iso-propyl, butyl, iso-butyl, sec-butyl, t-butyl group as well as pentyl, hexyl, heptyl or octyl group including their branched isomers; straight or branched alkenyl group, preferably having 2 to 8 carbon atoms such as vinyl, propenyl, butenyl, pentenyl, hexenyl, heptenyl or octenyl group.

Each values of $R_4$ and $R_5$ are same or different which include a hydrogen atom, straight or branched lower alkyl group having 1 to 4 carbon atoms as same as above-mentioned group which may optionally form a 3 to 6 membered ring by cyclization of $R_4$ and $R_5$.

Values of $R_6$ include a hydrogen atom; a straight or branched alkyl group, preferably having 1 to 8 carbon atoms such as methyl, ethyl, propyl, iso-propyl, butyl, iso-butyl, sec-butyl, t-butyl group as well as pentyl, hexyl, heptyl and octyl group including their branched isomer; a straight or branched alkynyl group preferably having 3 to 8 carbon atoms such as propynyl, butynyl, pentynyl, hexynyl, heptynyl and octynyl group; an aralkyl group which may optionally be substituted with halogen atom, alkyl, alkoxy or nitro group, such as benzyl, phenetyl, naphtylmethyl group; an acyl group including aliphatic acyl group such as acetyl, propionyl, butyryl, valeryl, acryloyl group, aromatic acyl group which may optionally be substituted with halogen atom, alkyl, alkoxy or nitro group, such as benzoyl, naphthoyl, cinnamoyl group, and heterocyclic acyl group such as furoyl or thenoyl group.

When A is a hydrogen atom and the broken line is no bond, the compounds of the present invention have 1,2,3,4-tetrahydroquinoline structure. When A is a hydrogen atom and the broken line is a second bond, the compounds of the present invention have 1,2-dihydroquinoline structure. When A is an oxo group, the compounds of the present invention have 4-oxo-1,2,3,4-tetrahydroquinoline structure.

Among the compounds of the present invention, the preferable compounds are as follows:

$R_1$ is a hydrogen atom, methyl or ethyl. Especially when $R_1$ is a pharmacologically acceptable alkyl group, some advantageous effects include reduction or inhibition of the gastro duodenum disorders upon administration of the present invention by injection or ingestion, and rapid absorption if administered by ointment. With respect to the process for producing the compounds, the above-mentioned lower alkyl groups having 1 to 4 carbon atoms are effective as a protecting group of carboxyl acids.

$R_2$ is a hydrogen atom or methyl group, $R_3$ is a hydrogen, fluorine, chlorine atom, propyl or allyl group, $R_4$ and $R_5$ are each hydrogen atom, methyl or ethyl group. $R_6$ is a hydrogen atom, methyl, ehtyl, propyl, butyl, allyl, methallyl, propargyl, benzyl, benzyl substituted with fluorine atom or 1 or 2 chlorine atoms, acetyl, benzoyl, toluoyl; benzoyl substituted with fluorine, 1 or 2 chlorine atoms or 1 or 2 methoxy groups.

When optical isomers exist in the above-mentioned compounds, the present invention includes any of the dl-, l- and d-isomers.

The present invention also includes pharmaceutically acceptable salts of the compounds, and those with alkali metals such as sodium, potassium and lithium, with alkaline-earth metals such as calcium and magnesium, with other metals such as aluminum, with ammonium, and with organic amines such as trimethylamine, triethylamine, pyrrolidone, piperidine, morpholine, pyridine, picoline, are especially preferred when the compounds are free carboxylic acids.

In accordance with the present invention, the new compounds are prepared as follows. The substituents have the same meanings as those in the above-mentioned general formula (I) unless otherwise stated.

(1) A compound represented by the general formula (II)

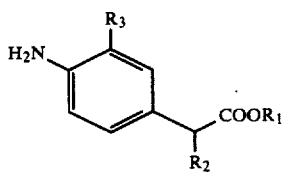

is reacted with a compound represented by the general formula (III)

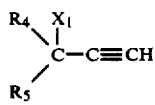

(wherein $X_1$ indicates a halogen atom) to give a compound represented by the general formula (IV)

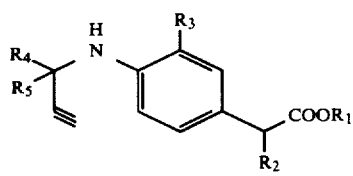

and the compound (IV) is converted to a compound represented by the general formula (I-1) by ring closure reaction.

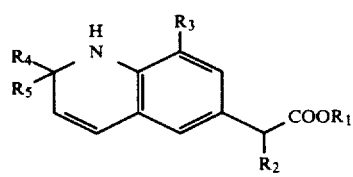

To carry out the reaction, the compounds represented by the general formula (II) and (III) are allowed to stand at between 0° C. and the boiling point of the reaction mixture with refluxing in an inert solvent such as tetrahydrofuran, dioxane, ether or mixtures of them and water, in the presence of a tertiary amine such as triethylamine, added copper(I) chloride; optionally with copper powder, to give the compound represented by the general formula (IV).

The compound of the general formula (IV) is an important intermediate of the present invention. The resultant compound (IV) is then heated in an inert solvent such as dioxane, tetrahydrofuran, dimethylformamide, dimethylsulfone, in the presence of metal halide such as copper(II) chloride, zinc chloride, or copper(II) chloride to yield by ring closure the intended compound.

(2) A compound represented by the general formula (I-2)

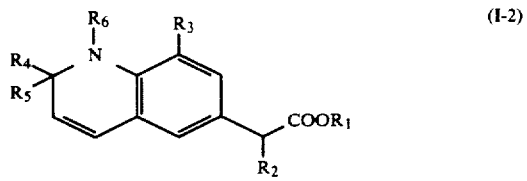

is easily converted to a compound represented by the general formula (I-3) by hydrogenation reaction.

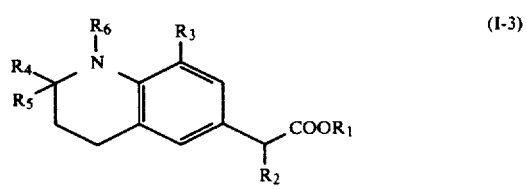

The hydrogenation reaction is carried out in an inert solvent, preferably a lower alcohol, in the presence of hydrogenation catalyst such as palladium-on-carbon, palladium black, platinum dioxide and Raney-Nickel. It is suitable to hydrogenate under hydrogen pressure that is ordinally atmospheric pressure or slightly pressured. When the reaction mixture is pressurized and heated, the reaction quickly proceeds.

When $R_3$, $R_6$ in the general formula (I-2) is an alkenyl or alkynyl group, these groups are converted to an alkyl group caused by the hydrogenation reaction.

(3) A compound represented by the general formula (I-4)

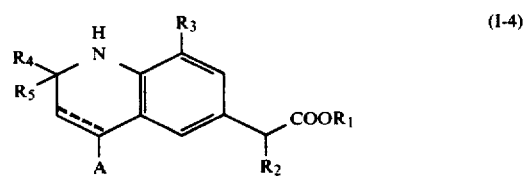

is reacted with a compound represented by the general formula (V)

(wherein $R_6$ is not a hydrogen atom, $X_2$ indicates a halogen atom, hydroxy group or active ester) to give a compound represented by the general formula (I-5).

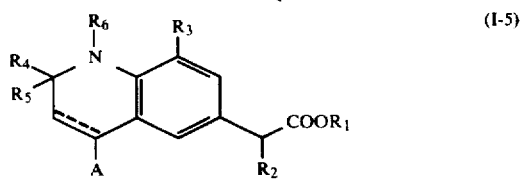

(wherein R₆ is not a hydrogen atom). This reaction is carried out in an inert solvent, preferably a non-protic polar solvent such as dimethylformamide and ketones, in the presence of a base such as potassium carbonate, with heating at an appropriate temperature. In this case, the yields of the products are elevated by the optional addition of potassium iodide. A basic solvent such as pyridine may also be used.

When X₂ is a hydroxy group, the compound (I-4) may be reacted in the presence of carbodiimides such as dicyclohexylcarbodiimide.

(4) A compound represented by the general formula (I-6)

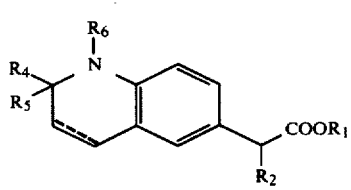

(wherein R₆ is an alkenyl group) is reacted by migration reaction in the presence of zinc chloride in an inert solvent such as dioxane or tetrahydrofuran with heating to give a compound represented by the general formula (I-7)

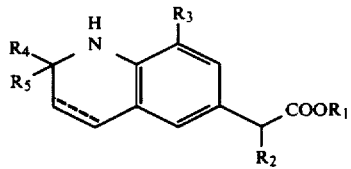

(wherein R₃ is an alkenyl group).

(5) The above-mentioned compound represented by the general formula (I-1) is heated in water or alcohols, preferably in alcohol corresponding to R₁, in the presence of catalyst such as palladium chloride to yield a compound represented by the general formula (I-8).

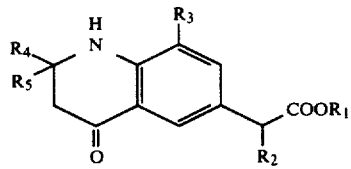

(6) The above-mentioned compound represented by the general formula (II) is heated with β-propiolactone in an inert solvent such as acetonitrile to give a compound represented by the general formula (VI).

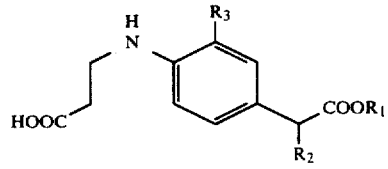

The resultant compound (VI) is then heated and ring closed in polyphosphoric acid as a sole solvent, optionally added xylene or toluene, to yield a compound represented by the general formula (I-8).

(7) The above-mentioned compound represented by the general formula (I-8) is converted by the reaction of "Wolf-Kishner reduction" to give a compound represented by the general formula (I-9).

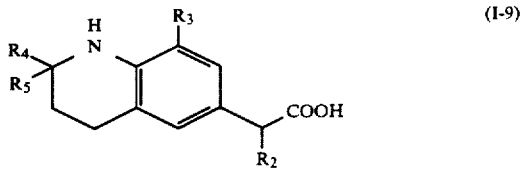

The compound (I-8) is heated with hydrazine hydrate or alkali hydroxide in a solvent, such as glycols or dimethyl sulfoxide.

The above-mentioned processes for producing the compounds of the present invention may be employed either alone or in combination according to the necessity. In each step of the processes the ester derivatives of which R₁ is an alkyl group are preferably used. The hydrolysis of the esters to obtain the corresponding free carboxylic acids of the present invention can be done by any well-known process, which is carried out in an appropriate solvent such as water, lower alcohols or mixtures of them, using a base such as sodium hydroxide, potassium hydroxide, sodium carbonate, potassium carbonate, sodium hydrogencarbonate or potassium hydrogencarbonate. In the case of benzyl ester derivatives, an ester moiety may be removed under reductive conditions, such as in the presence of palladium-on-carbon.

Further, the free carboxylic acids of the present invention are reacted with an alcohol corresponding to a selected R₁ in the presence of an acid such as sulfuric acid, hydrogen chloride, hydrochloric acid, p-toluenesulfonic acid, camphorsulfonic acid or thionyl chloride to give the ester derivatives of the present invention.

The compounds of the present invention also may be converted to their salts, if desired, in the usual ways.

The compounds of the present invention can be purified by usual methods such as distillation, chromatography and recrystallization. They are identified by, inter alia, elemental analysis, melting point, IR, NMR, UV and mass spectrum, etc.

The examples, which follow, describe the preparation of the compounds of the present invention.

EXAMPLE 1

9.3 g of Ethyl 2-(4-amino-3-chlorophenyl)propionate were dissolved in a mixture of 100 ml of dioxane and 30 ml of water. 1.0 g of copper(I) chloride and 10 ml of triethylamine were further added to the solution. 6.3 g of 3-chloro-3-methyl-1-butyn was added dropwise thereto with stirring under nitrogen atmosphere. The mixture was reacted at 5° C. for 2 hours, followed by addition of a mixture of hexane and water and then separation of the organic layer. The organic layer was washed with water and saturated aqueous solution of sodium chloride, dried over anhydrous magnesium sulfate, then the solvent was distilled off. The residue was purified by column chromatography on silica gel (eluted with benzene) to give 6.1 g of ethyl 2-[3-chloro-4-(1,1-dimethyl-2-propynylamino)phenyl]propionate (Compound 1).

In the same way, the following compounds were obtained:

Methyl 2-[4-(1,1-dimethyl-2-propynylamino)phenyl]-
propionate (Compound 2)

Methyl 2-[3-fluoro-4-(1,1-dimethyl-2-propynylamino)-
phenyl]propionate (Compound 3)

Ethyl 4-(1,1-dimethyl-2-propynylamino)phenylacetate
(Compound 4)

Ethyl 3-chloro-4-(1,1-dimethyl-2-propynylamino)phe-
nylacetate (Compound 5)

EXAMPLE 2

6.5 g of Ethyl 2-[3-chloro-4-(1,1-dimethyl-2-propynylamino)phenyl]propionate (Compound 1) was dissolved in 70 ml of dioxane, and 10.0 g of zinc chloride were added thereto. The mixture was reacted at 95° C. for 15 hours under nitrogen atmosphere. After the reaction, the mixture was diluted with 100 ml of hexane, and subjected to column chromatography on silica gel. The solvent was distilled off to give 6.1 g of Ethyl 2-(8-chloro-1,2-dihydro-2,2-dimethylquinolin-6-yl)propionate (Compound 6).

In the same way, the following compounds were obtained:

Methyl 2-(1,2-dihydro-2,2-dimethylquinolin-6-yl)pro-
pionate (Compound 7)

Methyl 2-(8-fluoro-1,2-dihydro-2,2-dimethylquinolin-6-
yl)propionate (Compound 8)

Ethyl 1,2-dihydro-2,2-dimethyl-6-quinolylacetate
(Compound 9)

Ethyl 8-chloro-1,2-dihydro-2,2-dimethyl-6-quinolylace-
tate (Compound 10)

EXAMPLE 3

3 g of methyl 2-(1,2-dihydro-2,2-dimethylquinolin-6-yl)propionate (Compound 7) were added to absolute ethanol. Palladium-on-carbon was further added to the solution, and the mixture was reacted with bubbling hydrogen gas at room temperature for 4 hours with stirring. After the reaction, the catalyst was filtered off and ethanol was distilled off to give 3.1 g of methyl 2-(1,2,3,4-tetrahydro-2,2-dimethylquinolin-6-yl)pro-
pionate (Compound 11).

In the same way, the following compounds were obtained:

Ethyl 2-(8-chloro-1,2,3,4-tetrahydro-2,2-dimethyl-
quinolin-6-yl)propionate (Compound 12)

Methyl 2-(8-fluoro-1,2,3,4-tetrahydro-2,2-dimethyl-
quinolin-6-yl)propionate (Compound 13)

EXAMPLE 4

3.7 g of methyl 2-(1-allyl-1,2-dihydro-2,2-dimethyl-quinolin-6-yl)propionate (Compound 20) was added to ethanol. Palladium-on-carbon was further added to the solution, and the mixture were reacted with stirring at room temperature for 20 hours under atmospheric pressure in hydrogen atmosphere. After the catalyst was filtered off, the filtrate was concentrated, and then purified by column chromatography on silica gel (ether:-hexane=1:4) to give 3.0 g of methyl 2-(1,2,3,4-tetrahy-dro-2,2-dimethyl-1-propylquinolin-6-yl)propionate (Compound 14).

In the same way, methy 2-(8-allyl-1,2-dihydro-2,2-dimethylquinolin-6-yl)propionate (Compound 30) is converted to methyl 2-(1,2,3,4-tetrahydro-2,2-dimethyl-8-propylquinolin-6-yl)propionate (Compound 15).

EXAMPLE 5

1.9 g of methyl 2-(1,2-dihydo-2,2-dimethylquinolin-6-yl)propionate (Compound 7) were added to 40 ml of acetone. 2.0 g of potassium carbonate and 2.0 ml of methyl iodide were added to the solution, and the mixture was heated and refluxed for 17 hours. After the mixture was cooled, the mixture was diluted with ether. Then the precipitate was filtered off, and the solvent was distilled off to give 1.9 g of methyl 2-(1,2-dihydro-1,2,2-trimethylquinolin-6-yl)propionate (Compound 16).

EXAMPLE 6

3.0 g of methyl 2-(1,2,3,4-tetrahydro-2,2-dimethyl-quinolin-6-yl)propionate (Compound 11) were added to 30 ml of pyridine, and 2.6 g of benzoyl chloride was further added to the solution. The mixture was stirred at room temperature for 15 hours, followed by addition of ice-water and extraction with ether. The ethereal solution was washed with 10% hydrochloric acid, water and saturated aqueous solution of sodium chloride, and dried over anhydrous sodium sulfate. Ether was distilled off to give 3.9 g of methyl 2-(1-benzoyl-1,2,3,4-tet-rahydro-2,2-dimethylquinolin-6-yl)propionate (Compound 17).

In the manner described in examples 5 and 6, the following compounds of the general formula (I-5) were obtained from the compounds corresponding to the general formula (I-4).

Ethyl 2-(8-chloro-1,2-dihydro-1,2,2-trimethylquinolin-
6-yl)propionate (Compound 18)

Methyl 2-(8-fluoro-1,2-dihydro-1,2,2-trimethylquinolin-
6-yl)propionate (Compound 19)

Methyl 2-(1-allyl-1,2-dihydro-2,2-dimethylquinolin-6-
yl)propionate (Compound 20)

Methyl 2-(1-allyl-1,2,3,4-tetrahydro-2,2-dimethylquino-
lin-6-yl)propionate (Compound 21)

Methyl 2-(1,2,3,4-tetrahydro-2,2-dimethyl-1-propargyl-
quinolin-6-yl)propionate (Compound 22)

Methyl 2-[1-(4-chlorobenzoyl)-1,2,3,4-tetrahydro-2,2-
dimethylquinolin-6-yl]propionate (Compound 23)

Methyl 2-(1-acetyl-1,2,3,4-tetrahydro-2,2-dimethyl-
quinolin-6-yl)propionate (Compound 24)

Methyl 2-[1,2,3,4-tetrahydro-2,2-dimethyl-1-(4-methyl-
benzoyl)quinolin-6-yl]propionate (Compound 25)

Methyl 2-[1,2,3,4-tetrahydro-1-(4-methoxybenzoyl)-2,2-
dimethylquinolin-6-yl]propionate (Compound 26)

Methyl 2-(1-benzyl-1,2,3,4-tetrahydro-2,2-dimethyl-
quinolin-6-yl)propionate (Compound 27)

Methyl 2-[1-(4-chloro-benzyl)-1,2,3,4-tetrahydro-2,2-
dimethylquinolin-6-yl]propionate (Compound 28)

Methyl 2-[1,2,3,4-tetrahydro-2,2-dimethyl-1-(2-methyl-
2-propenyl)quinolin-6-yl]propionate (Compound 29)

EXAMPLE 7

2.0 g of methyl 2-(1-allyl-1,2-dihydro-2,2-dimethyl-quinolin-6-yl)propionate (Compound 20) were added to 30 ml of dioxane. After 3.2 g of zinc chloride were further added to the solution, the mixture was heated and refluxed for 24 hours under nitrogen atmosphere. After cooling, hexane was filtered off and washed with benzene. The filtrate and the wash were combined and dried over anhydrous sodium sulfate. Then the solvent was removed, and the residue was subjected to column chromatography on silica gel and eluted with benzene to give 1.1 g of methyl 2-(8-allyl-1,2-dihydro-2,2-dime-thylquinolin-6-yl)propionate (Compound 30).

EXAMPLE 8

1.0 g of methyl 2-(8-chloro-1,2-dihydro-2,2-dimethyl-quinolin-6-yl)propionate was added to 20 ml of methanol. 2.0 g of palladium chloride was further added to the solution, and the mixture was stirred at 55°–60° C. for 6 hours. After cooling, 2 g of potassium carbonate and benzene were added to the mixture, then the mixture was further stirred. The precipitates were filtered off and washed with benzene. The filtrate and the wash were combined and concentrated, followed by addition of dilute aqueous solution of sodium hydrogencarbonate, and extraction with ether. The ethereal solution was washed with water, saturated aqueous solution of sodium sulfate and then the solvent was distilled off. The residue was purified by column chromatography on silica gel (benzene:ether=9:1) to give 0.3 g of methyl 2-(8-chloro-1,2,3,4-tetrahydro-2,2-dimethyl-4-oxoquinolin-6-yl)propionate (Compound 31).

EXAMPLE 9

20.1 g of methyl 2-(4-amino-3-chlorophenyl)propionate were added to 50 ml of acetonitrile. 6 ml of β-propiolactone were added dropwise to the solution with heating and refluxing, and the reaction was continued for 16 hours. After cooling, ice-water and aqueous solution of sodium hydroxide were added to the mixture and stirred, followed by wash with ether. The water layer was acidified with dilute hydrochloric acid and extracted with ether. The ethereal solution was washed with water and saturated aqueous solution of sodium chloride, and dried over anhydrous sodium chloride. The solvent was distilled off to give 18.4 g of methyl 2-4-(2-carboxyethylamino)-3-chlorophenyl propionate.

Further, the suspension of 80 g of polyphosphoric acid and 80 ml of toluene was stirred at 100° C., 20 ml of toluene solution of above-mentioned compound (methyl 2-[4-(2-carboxyethylamino)-3-chlorophenyl]-propionate) were added thereto and stirred for further 1 hour. After cooling, ice-water was added to the reaction mixture, then the mixture was poured into an aqueous solution of sodium hydroxide to adjust the pH to 9 to 10, followed by extraction with ethyl acetate. The organic layer was washed with water and saturated aqueous solution of sodium chloride, and dried over anhydrous sodium sulfate. The solvent was distilled off, and the residue was subjected to column chromatography on silica gel, eluted with a mixture of ether and hexane to give 6.4 g of methyl 2-(8-chloro-1,2,3,4-tetrahydro-4-oxoquinolin-6-yl)propionate (Compound 32).

EXAMPLE 10

3.0 g of methyl 2-(8-chloro-1,2,3,4-tetrahydro-4-oxoquinolin-6-yl)propionate (Compound 32) were added to 30 ml of trimethyleneglycol. 3.0 ml of hydrazine hydrate and 3 g of potassium hydroxide were added to the solution. The mixture was heated and stirred with removing azeotropic mixture of water and glycol at 150° C. for 1.5 hours and then at 230° C. for 4 hours. After cooling, the reaction mixture was poured into cold water and made acidic (pH 4–5) with hydrochloric acid, followed by extraction with ether.

The ethereal solution was washed with water and saturated aqueous solution of sodium chloride and, dried over anhydrous magnesium sulfate. The solvent was distilled off to give crystals of the desired compound. The crystals were recrystallized from a mixture of hexane and ethyl acetate to give 2.1 g of 2-(8-chloro-1,2,3,4-tetrahydroquinolin-6-yl)propionic acid (Compound 33).

EXAMPLE 11

3.0 g of ethyl 2-(8-chloro-1,2-dihydro-1,2,2-trimethylquinolin-6-yl)propionate (Compound 18) were added to a mixture of 40 ml of ethanol and 10% aqueous solution of sodium hydroxide. The solution was heated and refluxed for 4 hours. Ethanol was distilled off and the reaction mixture was diluted with water and washed with ether. The water layer was made weakly acidic by the addition of hydrochloric acid, and then extracted with ethyl acetate. The organic layer was washed with water and saturated aqueous solution of sodium chloride, and dried over anhydrous magnesium sulfate. The solvent was distilled off, and the residue was recrystallized from hexane to give 2.3 g of 2-(8-chloro-1,2-dihydro-1,2,2-trimethylquinolin-6-yl)propionic acid (Compound 34).

In the same way, the following free carboxylic acids were obtained from corresponding ester derivatives.

2-(8-Chloro-1,2-dihydro-2,2-dimethylquinolin-6-yl)propionic acid (Compound 35)

2-(8-Chloro-1,2,3,4-tetrahydro-2,2-dimethylquinolin-6-yl)propionic acid (Compound 36)

2-(1,2-Dihydro-1,2,2-trimethylquinolin-6-yl)propionic acid (Compound 37)

2-(1,2,3,4-Tetrahydro-2,2-dimethylquinolin-6-yl)propionic acid (Compound 38)

2-(1,2-Dihydro-2,2-dimethylquinolin-6-yl)propionic acid (Compound 39)

2-(8-Fluoro-1,2-dihydro-2,2-dimethylquinolin-6-yl)propionic acid (Compound 40)

2-(8-Fluoro-1,2,3,4-tetrahydro-2,2-dimethylquinolin-6-yl)propionic acid (Compound 41)

2-(8-Fluoro-1,2-dihydro-1,2,2-trimethylquinolin-6-yl)propionic acid (Compound 42)

2-(8-Chloro-1,2,3,4-tetrahydro-4-oxoquinolin-6-yl)propionic acid (Compound 43)

2-(8-Chloro-1,2,3,4-tetrahydro-2,2-dimethyl-4-oxoquinolin-6-yl)propionate acid (Compound 44)

2-(1-Allyl-1,2-dihydro-2,2-dimethylquinolin-6-yl)propionic acid (Compound 45)

2-(1,2,3,4-Tetrahydro-2,2-dimethyl-1-propylquinolin-6-yl)propinic acid (Compound 46)

2-(1-Allyl-1,2,3,4-tetrahydro-2,2-dimethylquinolin-6-yl)propionic acid (Compound 47)

2-(1,2,3,4-Tetrahydro-2,2-dimethyl-1-propargylquinolin-6-yl)propionic acid (Compound 48)

2-(1-Benzoyl-1,2,3,4-tetrahydro-2,2-dimethylquinolin-6-yl)propionic acid (Compound 49)

2-[1-(4-Chlorobenzoyl)-1,2,3,4-tetrahydro-2,2-dimethylquinolin-6-yl]propionic acid (Compound 50)

2-(1-Acetyl-1,2,3,4-tetrahydro-2,2-dimethylquinolin-6-yl)propionic acid (Compound 51)

2-[1,2,3,4-Tetrahydro-2,2-dimethyl-1-(4-methylbenzoyl)quinolin-6-yl]propionic acid (Compound 52)

2-[1,2,3,4-Tetrahydro-1-(4-methoxybenzoyl)-2,2-dimethylquinolin-6-yl]propionic acid (Compound 53)

2-(1-Benzyl-1,2,3,4-tetrahydro-2,2-dimethylquinolin-6-yl)propionic acid (Compound 54)

2-[1-(4-Chlorobenzyl)-1,2,3,4-tetrahydro-2,2-dimethylquinolin-6-yl]propionic acid (Compound 55)

2-[1,2,3,4-Tetrahydro-2,2-dimethyl-1-(2-methyl-2-propenyl)quinolin-6-yl]propionic acid (Compound 56)

2-(1,2,3,4-Tetrahydro-2,2-dimethyl-8-propylquinolin-6-yl)propionic acid (Compound 57)

2-(8-Allyl-1,2-dihydro-2,2-dimethylquinolin-6-yl)propionic aicd (Compound 58)

EXAMPLE 12

To 30 ml of benzene were added 3.2 g of 2-(1-benzyl-1,2,3,4-tetrahydro-2,2-dimethylquinolin-6-yl)propionic acid (Compound 54), 4,4 g of p-toluenesulfonic acid and 14.3 g of 4-chlorobenzyl alcohol. The solution was heated and refluxed with removing water. The reaction mixture was concentrated, followed by washed petroleum ether and addition of ethyl acetate. Then the mixture was washed with sodium hydrogencarbonate, water and saturated aqueous solution of sodium chloride, and dried over anhydrous sodium sulfate. The solvent was distilled off, and the residue was purified by column chromatography on silica gel (Hexan acetate) to give 3.7 g of 4-chlorobenzyl 2-(1-benzyl-1,2,3,4-tetrahydro-2,2-dimethylquinolin-6-yl)propionate (Compound 59).

The characteristic data of the present invention are listed in Table 1 and 2.

TABLE 1

| Compound | (Oily compound) N M R (CDCl$_3$, δ value) |
|---|---|
| 1 | 1.20 (t, 3H), 1.44 (d, 3H), 1.64 (s, 6H), 2.37 (s, 1H), 3.56 (q, 1H), 4.08 (q, 2H), 4.30 (b s, 1H), 6.95~7.40 (m, 3H) |
| 2 | 1.45 (d, 3H), 1.57 (s, 6H), 2.35 (s, 1H), 3.61 (q, 1H), 3.63 (s, 3H), 3.70 (b s, 1H), 6.75~7.20 (m, 4H) |
| 3 | 1.44 (d, 3H), 1.60 (s, 6H), 2.36 (s, 1H), 3.60 (q, 1H), 3.63 (s, 3H), 3.66 (b s, 1H), 6.80~7.40 (m, 3H) |
| 4 | 1.22 (t, 3H), 1.56 (s, 6H), 2.34 (s, 1H), 3.49 (s, 2H), 3.60 (b s, 1H), 4.12 (q, 2H), 6.75~7.25 (m, 4H) |
| 5 | 1.24 (t, 3H), 1.64 (s, 6H), 2.38 (s, 1H), 3.48 (s, 2H), 4.13 (q, 2H), 4.35 (b s, 1H), 6.90~7.40 (m, 3H) |
| 6 | 1.19 (t, 3H), 1.31 (s, 6H), 1.43 (d, 3H), 3.48 (q, 1H), 4.09 (q, 2H), 4.15 (d, 1H), 5.45 (d d, 1H), 6.18 (d, 1H), 6.70 (d, 1H), 6.97 (d, 1H) |
| 7 | 1.27 (s, 6H), 1.41 (d, 3H), 3.60 (q, 1H), 3.61 (s, 3H), 3.70 (b s, 1H), 5.42 6.21 (AB, 2H), 6.26~6.95 (m, 3H) |
| 8 | 1.30 (s, 6H), 1.42 (d, 3H), 3.58 (q, 1H), 3.60 (s, 3H), 5.45 (d, 1H), 6.18 (d d, 1H), 6.55~6.85 (m, 2H), 3.75 (b s, 1H) |
| 9 | 1.20 (t, 3H), 1.25 (s, 6H), 3.39 (s, 2H), 3.70 (b s, 1H), 4.10 (q, 2H), 5.40 (d, 1H), 6.18 (d, 1H), 6.20~6.90 (m, 3H) |
| 10 | 1.24 (t, 3H), 1.33 (s, 6H), 3.38 (s, 2H), 4.11 (q, 1H), 4.25 (b s, 1H), 5.48 (d d, 1H), 6.18 (d, 1H), 6.65 (d, 1H), 6.94 (d, 1H) |
| 11 | 1.18 (s, 6H), 1.42 (d, 3H), 1.65 (t, 2H), 2.74 (t, 2H), 3.24 (b s, 1H), 3.56 (q, 1H), 3.62 (s, 3H), 6.25~7.00 (m, 3H) |
| 12 | 1.20 (t, 3H), 1.22 (s, 6H), 1.41 (d, 3H), 1.68 (t, 2H), 2.76 (t, 2H), 3.51 (q, 1H), 4.10 (q, 2H), 6.80 (d, 1H), 7.00 (d, 1H) |
| 13 | 1.21 (s, 6H), 1.44 (d, 3H), 1.37 (t, 2H), 2.75 (t, 2H), 3.52 (q, 1H), 3.62 (s, 3H), 3.70 (b s, 1H), 6.58~6.85 (m, 2H) |
| 14 | 0.92 (t, 3H), 1.21 (s, 6H), 1.44 (d, 3H), 1.30~1.85 (m, 4H), 2.83 (t, 2H), 2.95~3.25 (m, 2H), 3.58 (q, 1H), 3.63 (s, 3H), 6.30~7.05 (m, 3H) |
| 15 | 0.98 (t, 3H), 1.20 (s, 6H), 1.44 (d, 3H), 1.30~1.90 (m, 4H), 2.20~2.50 (m, 2H), 2.76 (t, 2H), 3.55 (q, 1H), 3.50 (b s, 1H), 3.62 (s, 3H), 6.75 (b s, 2H) |
| 16 | 1.30 (s, 6H), 1.41 (d, 3H), 2.75 (s, 3H), 3.58 (q, 1H), 3.60 (s, 3H), 5.37, 6.18 (AB, 2H), 6.38 (d, 1H), 6.73 (d, 1H), 6.95 (d d, 1H) |
| 17 | 1.40 (d, 3H), 1.68 (s, 6H), 1.70~2.00 (m, 2H), 2.50~2.80 (m, 2H), 3.55 (q, 1H), 3.59 (s, 3H), 6.25~7.35 (m, 8H) |
| 18 | 1.23 (s, 6H), 1.24 (t, 3H), 1.46 (d, 3H), 2.55 (s, 3H), 3.60 (q, 1H), 4.14 (q, 2H), 5.65, 6.38 (AB, 2H), 6.88 (d, 1H), 7.15 (d, 1H) |
| 19 | 1.28 (s, 6H), 1.44 (d, 3H), 2.86 (d, 3H), 3.56 (q, 1H), 3.64 (s, 3H), 5.54 (d, 1H), 6.26 (d d, 1H), 6.60~6.90 (m, 2H) |
| 20 | 1.32 (s, 6H), 1.42 (d, 3H), 3.55 (q, 1H), 3.60 (s, 3H), 3.76~3.95 (m, 2H), 4.95~5.40 (m, 2H), 5.30, 6.14 (AB, 2H, 5.55~6.00 (m, 1H), 6.30~6.86 (m, 3H) |
| 21 | 1.21 (s, 6H), 1.43 (d, 3H), 1.79 (t, 2H), 2.76 (t, 2H), 3.58 (q, 1H), 3.63 (s, 3H), 3.70~3.90 (m, 2H), 4.95~5.35 (m, 2H), 5.60~6.20 (m, 1H), 6.30~7.05 (m, 3H) |
| 22 | 1.29 (s, 6H), 1.43 (d, 3H), 1.76 (t, 2H), 2.12 (t, 1H), 2.73 (t, 2H), 3.57 (q, 1H), 3.61 (s, 3H), 3.98 (d, 2H), 6.60~7.10 (m, 3H) |
| 23 | 1.41 (d, 3H), 1.68 (s, 6H), 1.65~1.95 (m, 2H), 2.55~2.85 (m, 2H), 3.56 (q, 1H), 3.61 (s, 3H), 6.25~7.30 (m, 7H) |
| 25 | 1.41 (d, 3H), 1.68 (s, 6H), 1.65~1.95 (m, 2H), 2.25 (s, 3H), 2.55~2.85 (m, 2H), 3.56 (q, 1H), 3.62 (s, 3H), 6.25~7.25 (m, 7H) |
| 26 | 1.41 (d, 3H), 1.67 (s, 6H), 1.65~1.95 (m, 2H), 2.55~2.85 (m, 2H), 3.56 (q, 1H), 3.62 (s, 3H), 3.73 (s, 3H), 6.30~7.35 (m, 7H) |
| 27 | 1.24 (s, 6H), 1.42 (d, 3H), 1.90 (t, 2H), 2.85 (t, 2H), 3.55 (q, 1H), 3.60 (s, 3H), 4.43 (s, 2H), 6.15~7.35 (m, 8H) |
| 28 | 1.22 (s, 6H), 1.41 (d, 3H), 1.88 (t, 2H), 2.82 (t, 2H), 3.54 (q, 1H), 3.60 (s, 3H), 4.37 (s, 2H), 6.05~7.30 (m, 7H) (mp 83-85° C.) |
| 29 | 1.19 (s, 6H), 1.42 (d, 3H), 1.75 (b s, 3H), 1.80 (t, 2H), 2.77 (t, 2H), 3.55 (q, 1H), 3.61 (s, 3H), 3.62 (b s, 2H), 4.75~4.95 (m, 2H), 6.15~7.00 (m, 3H) |
| 30 | 1.26 (s, 6H), 1.42 (d, 3H), 3.10~3.30 (m, 2H), 3.54 (q, 1H), 3.62 (s, 3H), 3.70 (b s, 1H), 4.90~5.30 (m, 2H), 5.42 (d, 1H), 5.60~6.15 (m, 1H), 6.22 (d, 1H), 6.73 (b s, 2H) |
| 31 | 1.35 (s, 6H), 1.45 (d, 3H), 2.60 (s, 2H), 3.65 (q, 1H), 3.66 (s, 3H), 4.68 (b s, 1H), 7.36 (d, 1H), 7.62 (d, 1H) |
| 32 | 1.44 (d, 3H), 2.65 (t, 2H), 3.25~3.80 (m, 3H), 3.60 (s, 3H), 5.05 (b s, 1H), 7.34 (d, 1H), 7.62 (d, 1H) |
| 59 | 1.23 (s, 6H), 1.40 (d, 3H), 1.88 (t, 2H), 2.83 (t, 2H), 3.54 (q, 1H), 4.38 (s, 2H), 5.03 (s, 2H), 6.0~7.4 (m, 12H) |

TABLE 2

| Compound | m.p. (°C.) | NMR (CDCl$_3$, δvalue) | IR (KBr, cm$^{-1}$) |
|---|---|---|---|
| 33 | 133~135 | 1.28 (d, 3H), 1.60~2.00 (m, 2H), 2.68 (t, 2H) 3.26 (t, 2H), 3.48 (q, 1H), 5.35 (bs, 1H), 6.75 (d, 1H), 6.90 (d, 1H), 12.0 (bs, 1H) (DMSO-d$_6$) | 3600~2300, 3300 2930, 1715, 1480 1180, 765, 615 |
| 34 | 86~87 | 1.22 (s, 6H), 1.48 (d, 3H), 2.53 (s, 3H), 3.62 (q, 1H), 5.65, 6.38 (AB, 2H), 6.87 (d, 1H), 7.15 (d, 1H), 10.50 (bs, 1H), | 3600~2300, 2960 1705, 1545, 1465 1450, 1405, 1215 890, 725 |
| 35 | 130~132 | 1.35 (s, 6H), 1.37 (d, 3H), 3.52 (q, 1H), 5.51 (d, 1H), 6.22 (d, 1H), 6.75 (d, 1H), | 3600~2300, 3400 1710, 1490, 1210 |

TABLE 2-continued

| Compound | m.p. (°C.) | NMR (CDCl₃, δvalue) | IR (KBr, cm⁻¹) |
|---|---|---|---|
| | | 6.98 (d, 1H), 4.5~6.5 (bs, 2H), (Acetone-d₆) | 665 |
| 36 | 155~158 | 1.22 (s, 6H), 1.44 (d, 3H), 1.67 (t, 2H), 1.22 (s, 6H), 1.44 (d, 3H), 1.67 (t, 2H), 2.76 (t, 2H), 3.54 (q, 1H), 6.80~7.05 (m, 2H), 7.40 (bs, 2H) | 3600~2300, 3420 3600~2300, 3420 1710, 1610, 1500 |
| 37 | 128~131 | 1.30 (s, 6H), 1.42 (d, 3H), 2.75 (s, 3H), 3.54 (q, 1H), 5.37, 6.17 (AB, 2H), 6.38 (d, 1H), 6.75 (d, 1H), 6.96 (dd, 1H) | 3500~2300, 1700 1650, 1602, 1495 1320, 1120 |
| 38 | 108~109 | 1.17 (s, 6H), 1.42 (d, 3H), 1.65 (t, 2H), 2.72 (t, 2H), 3.53 (q, 1H), 6.30~7.00 (m, 3H) | 3600~2300, 3260 2960, 2920, 1695 1605, 1502, 1160 800 |
| 40 | 127~130 | 1.30 (s, 6H), 1.42 (d, 3H), 3.52 (q, 1H), 5.44 (d, 1H), 6.18 (dd, 1H), 6.55~6.85 (m, 2H), 7.30 (bs, 2H) | 3600~2300, 3425 1705, 1635, 1580 1495, 1230, 725 670 |
| 41 | 154~156 | 1.24 (s, 6H), 1.36 (d, 3H), 1.68 (t, 2H), 2.76 (t, 2H), 3.56 (q, 1H), 4.95 (bs, 2H), 6.60~6.90 (m, 2H) (Acetone-d₆) | 3600~2300, 3440 1705, 1625, 1585 1510, 1230, 1160 805, 675 |
| 42 | 95~97 | 1.28 (s, 6H), 1.44 (d, 3H), 2.87 (d, 3H), 3.56 (q, 1H), 5.52 (d, 1H), 6.28 (dd, 1H), 6.60~6.95 (m, 2H), 10.70 (bs, 1H) | 3600~2300, 1705 1560, 1230 |
| 43 | 1585~1600 | 1.42 (d, 3H), 2.61 (t, 2H), 3.50~3.85 (m, 3H) 5.90 (bs, 1H), 7.42 (d, 1H), 7.63 (d, 1H) (Acetone-d₆) | 3600~2400, 3360 1720, 1640, 1615 1530, 975, 950 |
| 44 | 168~169 | 1.35 (s, 6H), 1.46 (d, 3H), 2.60 (s, 2H), 3.62 (q, 1H), 4.90 (bs, 1H), 7.38, 7.64 (AB, 2H), 10.80 (bs, 1H) | 3600~2300, 3380 1710, 1635, 1610 1510, 1195 |
| 45 | 98~100 | 1.32 (s, 6H), 1.41 (d, 3H), 3.52 (q, 1H), 3.75~3.95 (m, 2H), 4.90~5.35 (m, 2H), 5.45~6.00 (m, 1H), 5.70, 6.12 (AB, 2H), 6.27~6.95 (m, 3H), 10.30 (bs, 1H) | 3600~2300, 2970 1700, 1605, 1495 1335 |
| 46 | 128~130 | 0.92 (t, 3H), 1.20 (s, 6H), 1.45 (d, 3H), 1.50~2.00 (m, 4H), 2.72 (t, 2H), 2.95~3.25 (m, 2H), 3.56 (q, 1H), 6.40 (d, 1H), 6.80~7.10 (m, 2H), 10.60 (bs, 1H) | 3600~2300, 2960 1700, 1610, 1505 |
| 47 | 1115~113 | 1.20 (s, 6H), 1.44 (d, 3H), 1.78 (t, 2H), 2.76 (t, 2H), 3.55 (q, 1H), 3.75~3.90 (m, 2H) 4.95~5.40 (m, 2H), 5.60~6.20 (m, 1H), 6.35~7.05 (m, 3H), 10.80 (bs, 1H) | 3600~2300, 2970 1700, 1645, 1615 1505 |
| 48 | 1085~1105 | 1.28 (s, 6H), 1.44 (d, 3H), 1.74 (t, 2H), 2.10 (t, 1H), 2.72 (t, 2H), 3.56 (q, 1H), 3.95 (d, 2H), 6.60~7.15 (m, 3H), 11.40 (bs, 1H) | 3600~2300, 3300 1700, 1605, 1505 |
| 49 | 164~166 | 1.40 (d, 3H), 1.68 (s, 6H), 1.70~2.00 (m, 2H) 2.55~2.80 (m, 2H), 3.56 (q, 1H), 6.34 (d, 1H) 6.64 (dd, 1H), 6.90~7.40 (m, 6H), 10.15 (bs, 1H) | 3600~2300, 1730 1640, 1605, 1495 |
| 50 | 156~158 | 1.43 (d, 3H), 1.68 (s, 6H), 1.65~1.95 (m, 2H) 2.55~2.85 (m, 2H), 3.58 (q, 1H), 6.25~7.30 (m, 7H), 9.60 (bs, 1H) | 3600~2300, 1735 1700, 1645, 1605 1500 |
| 51 | 1465~148 | 1.46 (d, 3H), 1.59 (s, 6H), 1.50~1.80 (m, 2H) 2.10 (s, 3H), 2.45~2.75 (m, 2H), 3.70 (q, 1H) 6.75~7.25 (m, 3H), 10.65 (bs, 1H) | 3600~2300, 1710 1620, 1605, 1500 1375 |
| 52 | 155~156 | 1.41 (d, 3H), 1.68 (s, 6H), 1.65~1.95 (m, 2H) 2.23 (s, 3H), 2.55~2.85 (m, 2H), 3.56 (q, 1H) 6.36 (d, 1H), 6.55~7.25 (m, 6H), 9.86 (bs, 1H) | 3600~2300, 1695 1645, 1605, 1500 |
| 53 | 124~1255 | 1.42 (d, 3H), 1.67 (s, 6H), 1.65~1.95 (m, 2H) 2.55~2.85 (m, 2H), 3.60 (q, 1H), 3.71 (s, 3H) 6.30~7.30 (m, 7H), 8.95 (bs, 1H) | 3600~2300, 1695 1635, 1605, 1500 |
| 54 | 1625~1645 | 1.23 (s, 6H), 1.40 (d, 3H), 1.89 (t, 2H), 2.83 (t, 2H), 3.54 (q, 1H), 4.42 (s, 2H), 6.22 (d, 1H), 6.60~7.40 (m, 7H), 10.44 (bs, 1H) | 3600~2300, 1700 1615, 1505 |
| 55 | 157~159 (Dec.) | 1.21 (s, 6H), 1.40 (d, 3H), 1.87 (t, 2H), 2.81 (t, 2H), 3.52 (q, 1H), 4.36 (s, 2H), 6.14 (d, 1H), 6.70~6.95 (m, 2H), 7.05~7.30 (m, 4H), 11.16 (bs, 1H) | 3600~2300, 1710 1615, 1505 |
| 56 | 148~150 (Dec.) | 1.20 (s, 6H), 1.44 (d, 3H), 1.76 (bs, 3H), 1.81 (t, 2H), 2.78 (t, 2H), 3.56 (q, 1H), 3.62 (bs, 2H), 4.80~5.00 (m, 2H), 6.20~7.05 (m, 3H), 10.56 (bs, 1H) | 3600~2300, 1710 1660, 1615, 1510 |
| 57 | 83.5~85.5 | 0.98 (t, 3H), 1.20 (s, 6H), 1.44 (d, 3H), 1.30~1.80 (m, 4H), 2.20~2.45 (m, 2H), 2.75 (t, 2H), 3.53 (q, 1H), 6.75 (bs, 2H), 7.30 (bs, 2H) | 3600~2300, 3420 2960, 1695, 1605 1500 |
| 58 | — | 1.25 (s, 6H), 1.42 (d, 3H), 3.10~3.30 (m, 2H) 3.52 (q, 1H), 4.85~5.25 (m, 2H), 5.42 (d, 1H) 5.60~6.10 (m, 1H), 6.20 (d, 1H), 6.72 (bs, | 3600~2300, 3410 1705, 1640, 1590 1480 (neat) |

TABLE 2-continued

| Compound m.p. (°C.) | NMR (CDCl₃, δvalue) | IR (KBr, cm⁻¹) |
|---|---|---|
| | 2H), 7.30 (bs, 2H) | |

The compounds of the present invention have new structures different from conventional non-steroid compounds and remarkably potent antiinflammatory, analgesic and antipyretic properties as well as low toxicity.

The following descriptions serve to illustrate animal studies.

(1) Acute toxicity

Groups of 10 male dd mice weighing some 18 g were orally administered the examined drugs and the number of death p 72 hours later was recorded.

An example of results is shown in Table 3.

TABLE 3

| Drugs | dosage (mg/kg) | Mortality (%) |
|---|---|---|
| Aminopyrine | 600 | 20 |
| | 800 | 100 |
| Phenylbutazone | 400 | 30 |
| | 600 | 100 |
| Compound 35 | 400 | 0 |
| | 800 | 20 |
| Compound 36 | 400 | 0 |
| | 800 | 10 |

(2) Inhibition of plantar edema induced by carrageenin 60 minutes after the drugs had been orally administered to groups of 7 Wister rats, 0.1 ml of 1% carrageenin solution was injected subcutaneously into the sole. The volume of the hind food was determined thereafter at intervals. The rate of increase in volume compared with the volume before carrageenin treatment was regarded as edema rate.

An example of the results is shown in FIG. 1.

Furthermore, sections of the stomach and intestinal tracts of the rats after the above-mentioned observation was made revealed mucosal disorder or formation of ulcer in the phenylbutazone administered group, while no abnormality was found in any animals in the group which received the compounds of the present invention.

(3) Analgesic effects by a modified Haffner method

Group of 10 dd mice were orally administered the examined drugs and 30 minutes later 2 mg/kg of morphine hydrochloride, the threshold dose, was injected subcutaneously. At 15, 30, 45 and 60 minutes thereafter, the root of mouse's tail was squeezed with a Kocher's forceps. The number of animals that did not exhibit pseudopain reactions was recorded and the determination with the largest number of responding animals among the four determinations was used for evaluation.

An example of results is shown in Table 4.

TABLE 4

| | Analgesic effects (%) | |
|---|---|---|
| Drugs | 100 mg/kg | 200 mg/kg |
| Aminopyrine | 30 | 35 |
| Compound 35 | 35 | 50 |
| Compound 36 | 30 | 55 |

(4) Analgesic effects by acetic acid writhing test 30 minutes after the examined drug was orally given, 0.1 ml/10 g of 0.6% acetic acid solution was intraperitoneally administered to group of 10 male dd mice weighing some 18 g. The number of stretching was calculted during an observation period of 15 to 20 minutes after acetic acid treatment. The average inhibition rate of stretching among 8 animals was regarded as the inhibition rate of the drug, excluding 2 animals showing maximum and minimum numbers of stretching.

An example of results is shown in Table 5.

TABLE 5

| | Analgesic effects (%) | | |
|---|---|---|---|
| Drugs | 50 mg/kg | 100 mg/kg | 150 mg/kg |
| Aminopyrine | 14 | 47 | 60 |
| Compound 35 | 37 | 52 | 68 |
| Compound 36 | 36 | 61 | 73 |

As above-mentioned animal experiments clearly indicate, the compounds of the present invention have excellent antiinflammatory and antipyretic actions. Therefore, these compounds are therapeutically valuable antiinflammatory, analgesic and antipyretic agents against various inflammations such as those in rheumatic diseases, arthritis, and other inflammations having a variety of redness, fever, swelling and pain, against painful diseases and manifestations such as acute and chronic pains, neuralgia, pains accompanied by inflammation, trauma and lumbago, and against a variety of symptoms having fever.

Although the test data presented in this application relate primarily to rats and mice, the compounds of the present invention are equally applicable to all mammals such as dogs, cats, monkeys, apes and man.

The compounds of the present invention can be made into pharmaceuticals by combination with appropriate medical carriers or diluents, and dosage forms of solids, semisolids, liquids or gases can be prepared in a usual way for oral or non-oral administrations.

On preparation of pharmaceutical dosage forms, the compounds of the present invention may be used in the form of their pharmaceutically acceptable salts, and they also can be used alone or in appropriate association thereof, as well as in combination with other pharmaceutically active components.

When the compounds are applied orally, they may be used alone or combined with appropriate fillers to make tablets or capsules, e.g. with conventional bases such as lactose, mannitol, corn starch, potato starch, with binders such as crystalline cellulose, cellulose derivatives, acacia, corn starch or gelatin, with disintegrators such as corn starch, potato starch or sodium carboxymethylcellulose, and with lubricants such as talc and magnesium stearate. They also can be combined with ointment bases such as vaseline, paraffin, plastibase, simple ointment, hydrophilic ointment, hydrophilic petrolatum and hydrophilic plastibase to make ointments.

Further, the compounds of the present invention may be mixed thoroughly with a variety of bases such as emulsifying bases or water-soluble bases to give suppositories.

As regards injectable forms, the compounds of the present invention can be administered as solutions or suspensions in aqueous solvents or non-aqueous solvents such as vegetable oils, synthetic aliphatic acid glycerides, esters of higher aliphatic acids and propylene glycol.

When utilized as inhalation or aerosol preparations, the compounds of the present invention in the form of a liquid or minute powder can be filled up in an aerosol container, with gas or liquid spraying agents, and with conventional adjuvants such as humidifying or dispersing agents added, if necessary. The compounds of the present invention also may be applied as pharmaceuticals for non-pressurized preparations such as nebulizer and atomizer. Poultices can be prepared by mixing the compounds with mentha oil, concentrated glycerin, kaolin of other suitable additives.

The desirable dose of the compounds of the present invention varies with the subject, method and period of administration, but generally it is recommended to administer orally 10 to 3,000 mg of these compounds daily to an adult to obtain the desired effects. One to several units of the unit preparation containing the compounds of the present invention in appropriate amount may be administered. As for non-oral administration (e.g. for injectional forms), doses in the order of one tenth to one third of the above oral dose are desirable as daily doses.

Some prescriptions of the pharmaceutical compositions are shown below as examples which contain the compounds of the present invention as active ingredients.

| Prescription example 1. (tablet) | |
|---|---|
| Components | Content of a tablet (mg) |
| an invented compound | 50 |
| lactose | 145 |
| corn starch | 55 |
| magnesium stearate | 10 |
| total | 260 mg |

| Prescription example 2. (capsule) | |
|---|---|
| Components | Content of a capsule (mg) |
| an invented compound | 100 |
| lactose | 200 |
| total | 300 mg |

| Prescription example 3. (injection) | |
|---|---|
| Components | Content of an ampoule (mg) |
| an invented compound | 10 |
| sodium chloride | proper amount |
| distilled water for injection | proper amount |
| total | 1 ml |

| Prescription example 4. (ointment) | |
|---|---|
| Components | Weight (g) |
| an invented compound | 1 |
| emulsified wax | 30 |
| white petrolatum | 50 |
| liquid parafin | 20 |
| total | 101 g |

| Prescription example 5. (suppository) | |
|---|---|
| Components | Content of a suppository (mg) |
| an invented compound | 20 |
| cacao butter | 1980 |
| total | 2000 mg |

BRIEF DESCRIPTION OF THE DRAWINGS

FIG. 1 illustrates antiinflammatory effects of the compounds of the present invention.

What is claimed is:

1. A quinolylacetic acid compound of the general formula (I)

(I)

wherein:

$R_1$ is hydrogen or an alkyl group having 1 to 4 carbon atoms;

$R_2$ is an alkyl group of 1 to 4 carbon atoms;

$R_3$ is a halogen, an alkyl group having 1 to 8 carbon atons, or an alkenyl group having 2 to 8 carbon atons; and $R_4$ and $R_5$ are each an alkyl group having 1 to 4 carbon atoms or $R_4$ and $R_5$ can form a carbocyclic ring having 3 to 6 carbon atoms;

and pharmaceutically acceptable salts thereof.

2. The quinolylacetic acid compound of claim 1 wherein $R_2$ is a methyl group.

3. The quinolylacetic acid compound of claim 1 wherein $R_3$ is a methyl group.

4. The quinolylacetic acid compound of claim 1 wherein $R_4$ and $R_5$ are each a methyl group.

5. The quinolylacetic acid compound of claim 1 which is 2-(8-chloro-1,2,3,4-tetrahydro-2,2-dimethyl-quinolin-6-yl)propionic acid and pharmaceutically acceptable salts thereof.

6. The quinolylacetic acid compound of claim 1 which is 2-(8-fluoro-1,2,3,4-tetrahydro-2,2-dimethyl-quinolin-6-yl)propionic acid and pharmaceutically acceptable salts thereof.

7. A quinolylacetic acid compound of general formula (II)

(II)

wherein:

$R_1$ is hydrogen or an alkyl group having 1 to 4 carbon atoms;

$R_2$ is an alkyl group of 1 to 4 carbon atoms;

$R_3$ is hydrogen, a halogen, an alkyl group of 2 to 8 carbon atoms, or an alkenyl group of 2 to 8 carbon atoms;

$R_4$ and $R_5$ are each an alkyl group having 1 to 4 carbon atoms or $R_4$ and $R_5$ can form a carbocyclic ring having 3 to 6 carbon atoms; and $R_6$ is hydrogen, an alkyl group having 1 to 8 carbon atoms, an alkenyl group having 2 to 5 carbon atoms or an alkynyl group having 3 to 8 carbon atoms;

and further wherein at least one of $R_3$ and $R_6$ is other than hydrogen;

and pharmaceutically acceptable salts thereof.

8. The quinolylacetic acid compound of claim 7 wherein $R_2$ is a methyl group.

9. The quinolylacetic acid compound of claim 7 wherein $R_3$ is hydrogen, chlorine, or fluorine.

10. The quinolylacetic acid compound of claim 34 wherein $R_4$ and $R_5$ are each a methyl group.

11. The quinolylacetic acid compound of claim 7 wherein $R_6$ is hydrogen, a methyl group or an allyl group.

12. The quinolylacetic acid compound of claim 7 which is 2-(8-chloro-1,2-dihydro-2,2-dimethylquinolin-6-yl)propionic acid and pharmaceutically acceptable salts thereof.

13. The quinolylacetic acid compound of claim 7 which is 2-(8-chloro-1,2-dihydro-1,2,2-trimethylquinolin-6-yl)propionic acid and pharmaceutically acceptable salts thereof.

14. The quinolylacetic acid compound of claim 7 which is 2-(8-fluoro-1,2-dihydro-2,2-dimethylquinolin-6-yl)propionic acid and pharmaceutically acceptable salts thereof.

15. The quinolylacetic acid compound of claim 7 which is 2-(8-fluoro-1,2-dihydro-1,2,2-trimethylquinolin-6-yl)propionic acid and pharmaceutically acceptable salts thereof.

16. The quinolylacetic acid compound of claim 7 which is 2-(1-allyl-1,2-dihydro-2,2-dimethylquinolin-6-yl)propionic acid, and pharmaceutically acceptable salts thereof.

17. The quinolylacetic acid compound of claim 7 which is 2-(1-2-dihydro-1,2,2-trimethylquinolin-6-yl)propionic acid and pharmaceutically acceptable salts thereof.

18. An anti-inflammatory, anti-pyretic, and analgesic agent which comprises a carrier and at least one quinolylacetic acid compound according to any one of claims 1 through 17.

19. A method for treating inflammation or pain which comprises administering an effective amount of an anti-inflammatory, anti-pyretic and analgesic agent comprising a carrier and at least one quinolylacetic acid compound according to any one of claims 1 through 17.

* * * * *

UNITED STATES PATENT AND TRADEMARK OFFICE
CERTIFICATE OF CORRECTION

PATENT NO. : 4,555,513

DATED : November 26, 1985

INVENTOR(S) : Masaaki Hamada et al.

It is certified that error appears in the above-identified patent and that said Letters Patent is hereby corrected as shown below:

Column 18, line 67, "claim 34" should be --claim 7--.

Signed and Sealed this

Eighteenth Day of February 1986

[SEAL]

Attest:

DONALD J. QUIGG

Attesting Officer     Commissioner of Patents and Trademarks